(12) United States Patent
Chang et al.

(10) Patent No.: US 8,300,976 B2
(45) Date of Patent: Oct. 30, 2012

(54) SYSTEM AND METHOD FOR ADJUSTING BACKLIGHT IN MEASUREMENT OF A PROFILE IMAGE

(75) Inventors: Chih-Kuang Chang, Taipei Hsien (TW); Xian-Yi Chen, Shenzhen (CN); Zhong-Kui Yuan, Shenzhen (CN); Li Jiang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 978 days.

(21) Appl. No.: 12/344,252

(22) Filed: Dec. 25, 2008

(65) Prior Publication Data

US 2009/0317018 A1    Dec. 24, 2009

(30) Foreign Application Priority Data

Jun. 20, 2008   (CN) .......................... 2008 1 0302252

(51) Int. Cl.
*G06K 9/40*   (2006.01)

(52) U.S. Cl. ...................................................... 382/274

(58) Field of Classification Search ................... 382/141, 382/270, 272, 274; 250/205; 372/29.014; 396/164; 369/116; 209/581, 582
See application file for complete search history.

(56) References Cited

U.S. PATENT DOCUMENTS

| | | | | |
|---|---|---|---|---|
| 5,631,976 | A * | 5/1997 | Bolle et al. | 382/174 |
| 6,542,180 | B1 * | 4/2003 | Wasserman et al. | 348/131 |
| 2002/0074480 | A1 * | 6/2002 | Wasserman | 250/205 |
| 2003/0035061 | A1 * | 2/2003 | Iwaki et al. | 348/371 |
| 2007/0237363 | A1 * | 10/2007 | Hagio et al. | 382/106 |

* cited by examiner

*Primary Examiner* — Chan S Park
*Assistant Examiner* — Shervin Nakhjavan
(74) *Attorney, Agent, or Firm* — Altis Law Group, Inc.

(57) ABSTRACT

A computer-implemented method for adjusting backlight in measurement of a profile image of an object includes setting a light source of an image measuring machine to an original intensity level, obtaining the profile image of the object laid on the image measuring machine, and performing a mean filter processing and a binary image processing on the profile image. The method further includes setting intensity variables to adjust backlight intensity of the light source, uses the intensity variables to calculate an optimum intensity level of the backlight intensity utilizing an iterative method, and adjusting the backlight intensity of the light source to the optimum intensity level to obtain an optimum profile image of the object.

19 Claims, 5 Drawing Sheets

SYSTEM AND METHOD FOR ADJUSTING BACKLIGHT IN MEASUREMENT OF A PROFILE IMAGE

BACKGROUND

1. Field of the Invention

Embodiments of the present disclosure relate to systems and methods for adjusting light sources in measurement of object images, and more particularly, to a system and method for adjusting backlight in measurement of a profile image.

2. Description of Related Art

Product quality has long been one of the most important factors in maintaining a typical manufacturing enterprise's competitiveness. Ways of improving the quality of products is an important ongoing pursuit of such enterprises. It is essential to verify the correctness of an object before a batch production of the object. In recent years, a user can use an image measuring machine installed with a charge coupled device (CCD) to obtain a profile image of an object by scanning the object. In the measuring method, backlight source adjusting, which is usually performed by a user, is an essential problem in the measuring procedure. In normal cases, when the user adjusts the backlight source to measure the profile image of the object, errors are often occurred, and labor intensity of the user is high.

What is needed, therefore, is a system and method for adjusting backlight in measurement of the profile image, so as to overcome the above-described shortcomings.

DETAILED DESCRIPTION OF CERTAIN INVENTIVE EMBODIMENTS

All of the processes described below may be embodied in, and fully automated via, software code modules executed by one or more general purpose computers or processors. The code modules may be stored in any type of computer-readable medium or other computer storage device. Some or all of the methods may alternatively be embodied in specialized computer hardware.

Figure 1:
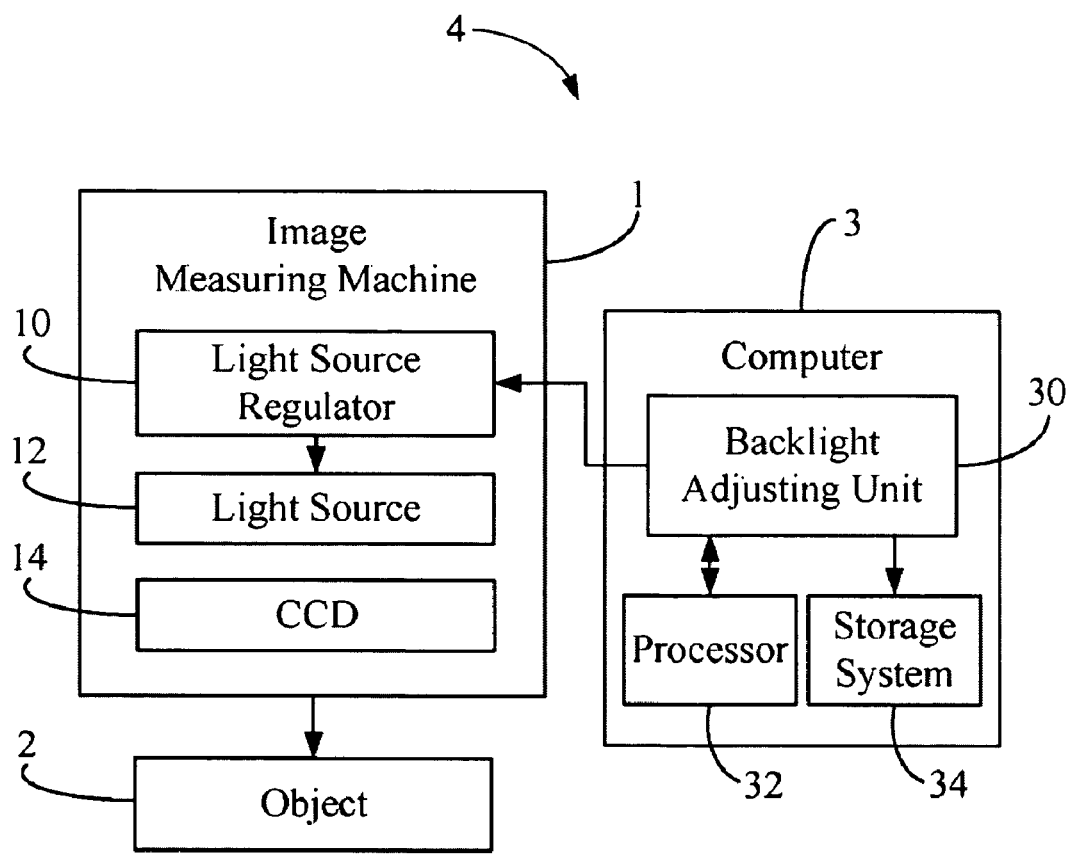
FIG. 1 is a block diagram of one embodiment of a system for adjusting backlight in measurement of a profile image.

FIG. 1 is a block diagram of one embodiment of a system 4 for adjusting backlight in measurement of a profile image (hereinafter, "the system 4"). In one embodiment, the system 4 includes an image measuring machine 1, an object 2 laid on a platform of the image measuring machine 1, and a computer 3 electrically connected with the image measuring machine 1. The image measuring machine 1 typically includes a light source regulator 10, a light source 12 and a charge coupled device (CCD) 14. The CCD 14 is configured for obtaining a profile image of the object 2 by scanning the object 2 using backlight emitted from the light source 12. The light source regulator 10 is configured for adjusting the light source 12 to emit the backlight for scanning the object 2 during the time when the CCD 14 captures the profile image of the object 2. The computer 3 comprises a backlight adjusting unit 30, at least one processor 32, and a storage system 34. The backlight adjusting unit 30 is configured for controlling the light source regulator 10 to adjust the backlight emitted from the light source 12 to an optimum intensity level in measurement of the profile image of the object 2.

In one embodiment, the light source 12 adopts 101 intensity levels to reflect the backlight intensity. The 101 intensity levels are ranging from 0-100 intensity levels.

Figure 2:
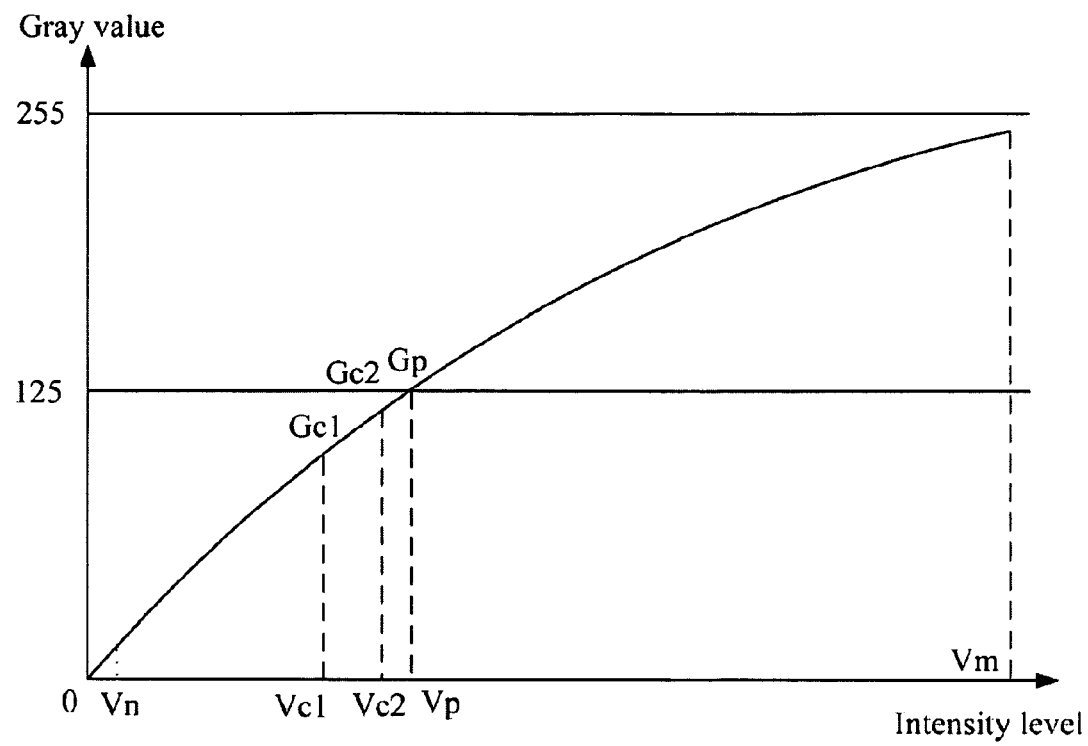
FIG. 2 is a schematic and graph diagram of gray values for different intensity levels of backlight intensity.

In another embodiment, the backlight intensity can be expressed by gray values of the profile image. Generally, a maximum distribution range of the gray values is [0, 255] (i.e., in the range from about 0 to about 255). In the embodiment, if the light source 12 is adjusted to the level 0, the profile image may be black, the backlight intensity is low, and the gray value of the profile image is about 0; otherwise, if the light source 12 is adjusted to the level 100, the profile image may be white, the backlight intensity is high, and the gray value of the profile image is about 255. See FIG. 2, which shows a schematic and graph diagram of the gray values for different intensity levels of the backlight intensity. In FIG. 2, the horizontal axis represents the intensity levels of the backlight intensity, and the vertical axis represents the gray values of the profile image. In the embodiment, FIG. 2 will be explained in greater detail in FIG. 5.

Figure 3:
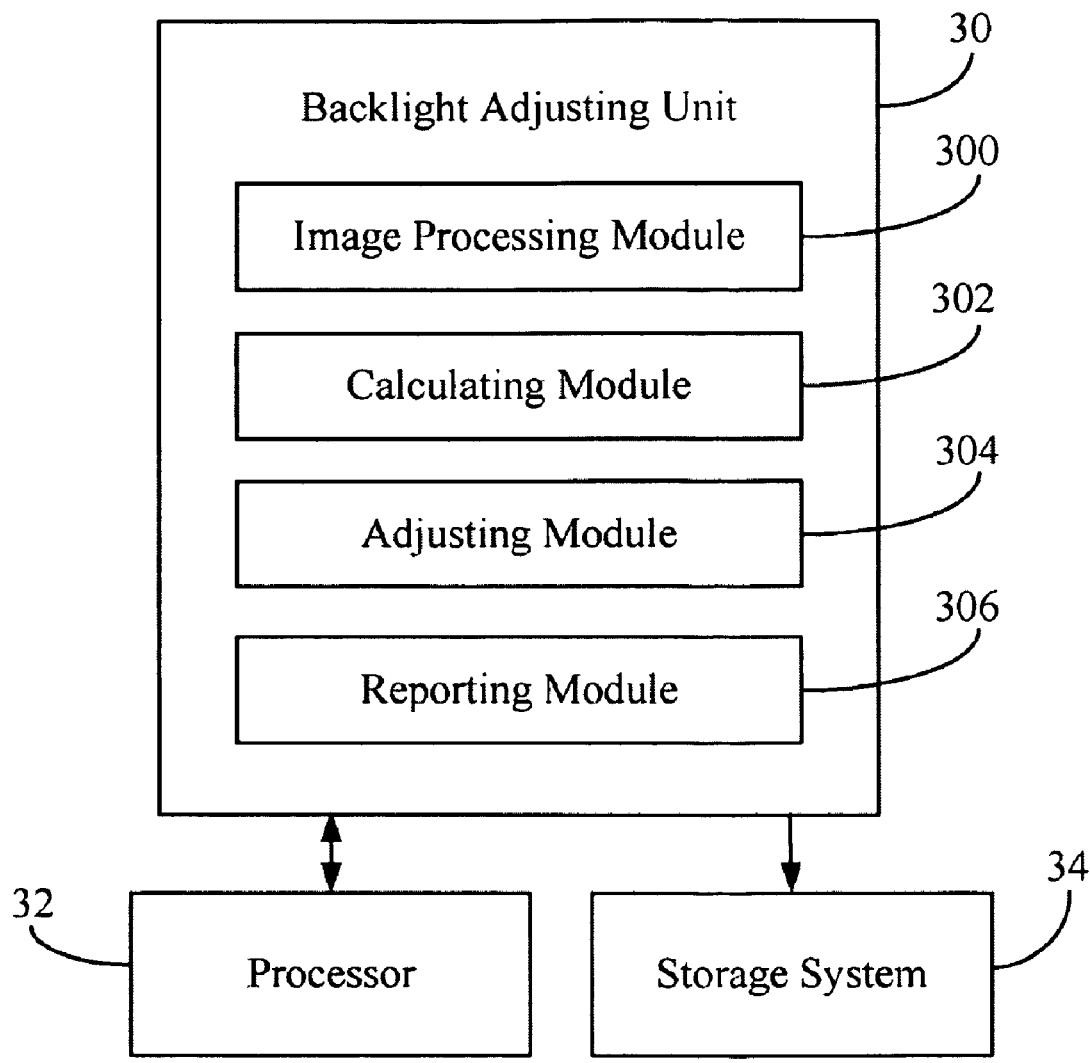
FIG. 3 is a block diagram of one embodiment of a backlight adjusting unit of FIG. 1.

FIG. 3 is a block diagram of one embodiment of the backlight adjusting unit 30 of FIG. 1. The backlight adjusting unit 30 may include a plurality of instructions, and executed by the processor 32 of the computer 3. In one embodiment, the backlight adjusting unit 30 may include an image processing module 300, a calculating module 302, an adjusting module 304, and a reporting module 306.

The image processing module 300 is configured for performing a mean filter processing and a binary image processing on a profile image of the object 2 after a user uses the light source regulator 10 to adjust the backlight intensity of the light source 12 to an original intensity level. In the embodiment, the mean filter processing and binary image processing are used for enhancing the contrast of the profile image, reducing image noises of the profile image, and eliminating uneven gray-level distribution.

The calculating module 302 is configured for setting a plurality of intensity variables to adjust the backlight intensity of the light source 12, and using the intensity variables to calculate an optimum intensity level of the backlight intensity by utilizing an iterative method. It may be understood that the iterative method is defined as solving a problem (for example an equation or system of equations) by finding successive approximations to the solution starting from an initial guess. The solution may be the optimum intensity level calculation, and the initial guess may be the original intensity level. In the embodiment, the intensity variables may include an upper approach level and a lower approach level as will be explained in greater detail below.

The adjusting module 304 is configured for adjusting the backlight intensity of the light source 12 to the optimum intensity level for obtaining an optimum profile image of the object 2.

The reporting module 306 is configured for storing the optimum profile image and the optimum intensity level into the storage system 34 of the computer 3, and reporting and displaying the optimum profile image. In one embodiment, the storage system 34 is at least one of a hard disk drive, a compact disc, a digital video disc, and a tape drive. The optimum profile image may be output and displayed on a display of the computer 3 to the user.

Figure 4:
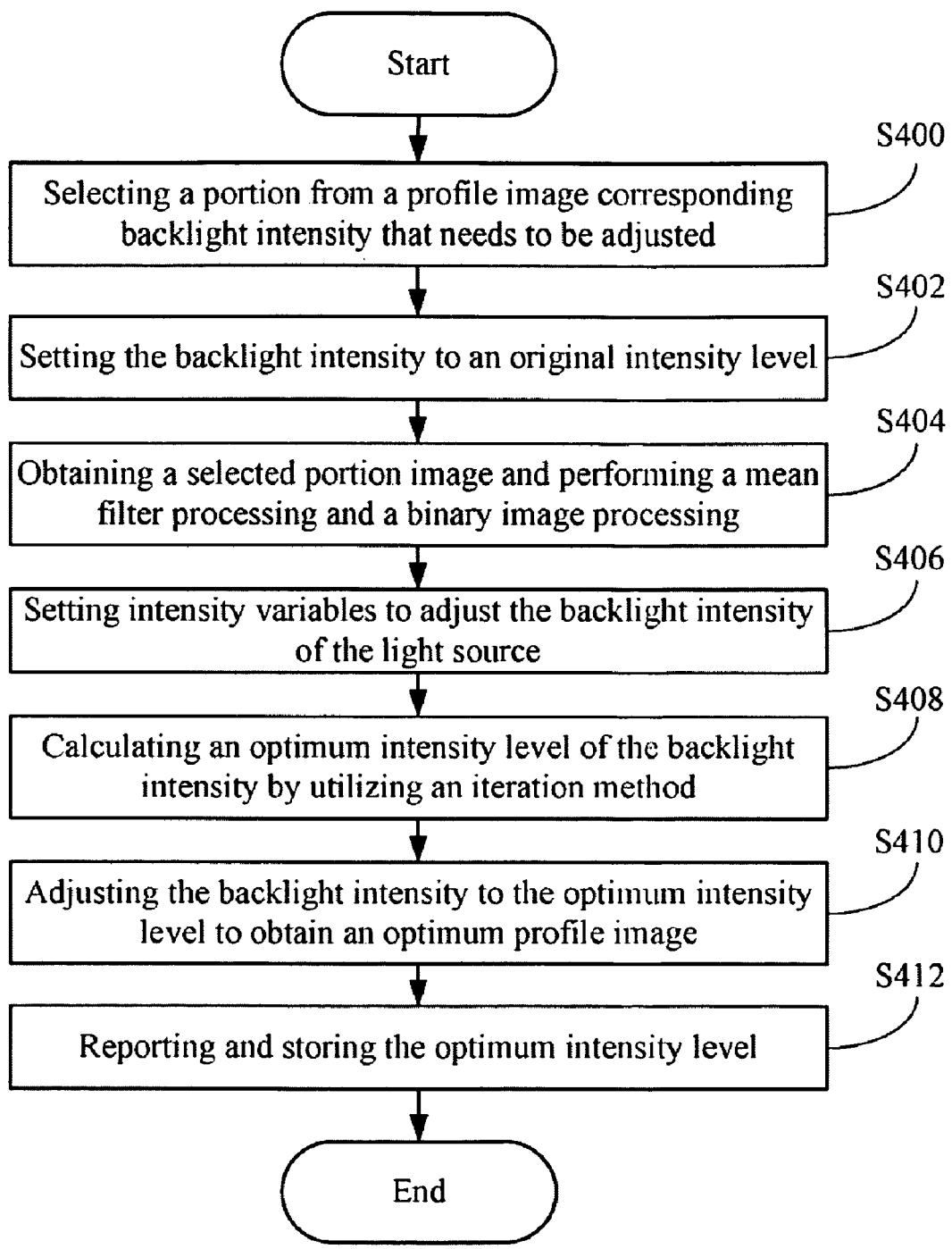
FIG. 4 is a flowchart of one embodiment of a method for adjusting backlight in measurement of a profile image.

FIG. 4 is a flowchart of one embodiment of a method for adjusting backlight in measurement of a profile image. Depending on the embodiment, additional blocks may be added, while others removed, and the ordering of the blocks may also be changed.

In block S400, the CCD 14 obtains a profile image of the object 2 that is laid on a platform of the image measuring machine 1, and selects a portion from the profile image corresponding the backlight intensity that needs to be adjusted.

In block S402, the adjusting module 304 controls the light source regulator 10 to set backlight intensity of the light source 12 to an original intensity level. In the embodiment, the original intensity level is in the range from the levels 0-100 intensity levels, but cannot be the level 0 or the level 100. The present embodiment gives an example that the original intensity level equals the level 10.

In block S404, the image processing module 300 obtains the selected portion image, and performs the mean filter processing and binary image processing on the portion image, in order to enhance a contrast of the portion image, reduce image noises of the portion image, and eliminate uneven gray-level distribution of the portion image.

In block S406, the calculating module 302 sets a plurality of intensity variables for adjusting the backlight intensity of the light source 12. The intensity variables may include an upper approach level and a lower approach level.

In block S408, the calculating module 302 uses the intensity variables to calculate an optimum intensity level of the backlight intensity by utilizing an iterative method. The iterative method will be described in the following FIG. 5.

In block S410, the adjusting module 304 controls the light source regulator 10 to adjust the backlight intensity of the light source 12 to the optimum intensity level, and the CCD 14 obtains an optimum profile image from the portion image.

In block S412, the reporting module 306 reports and displays the optimum profile image, and stores the optimum profile image and the optimum intensity level into the storage system 34 of the computer 3.

Figure 5:
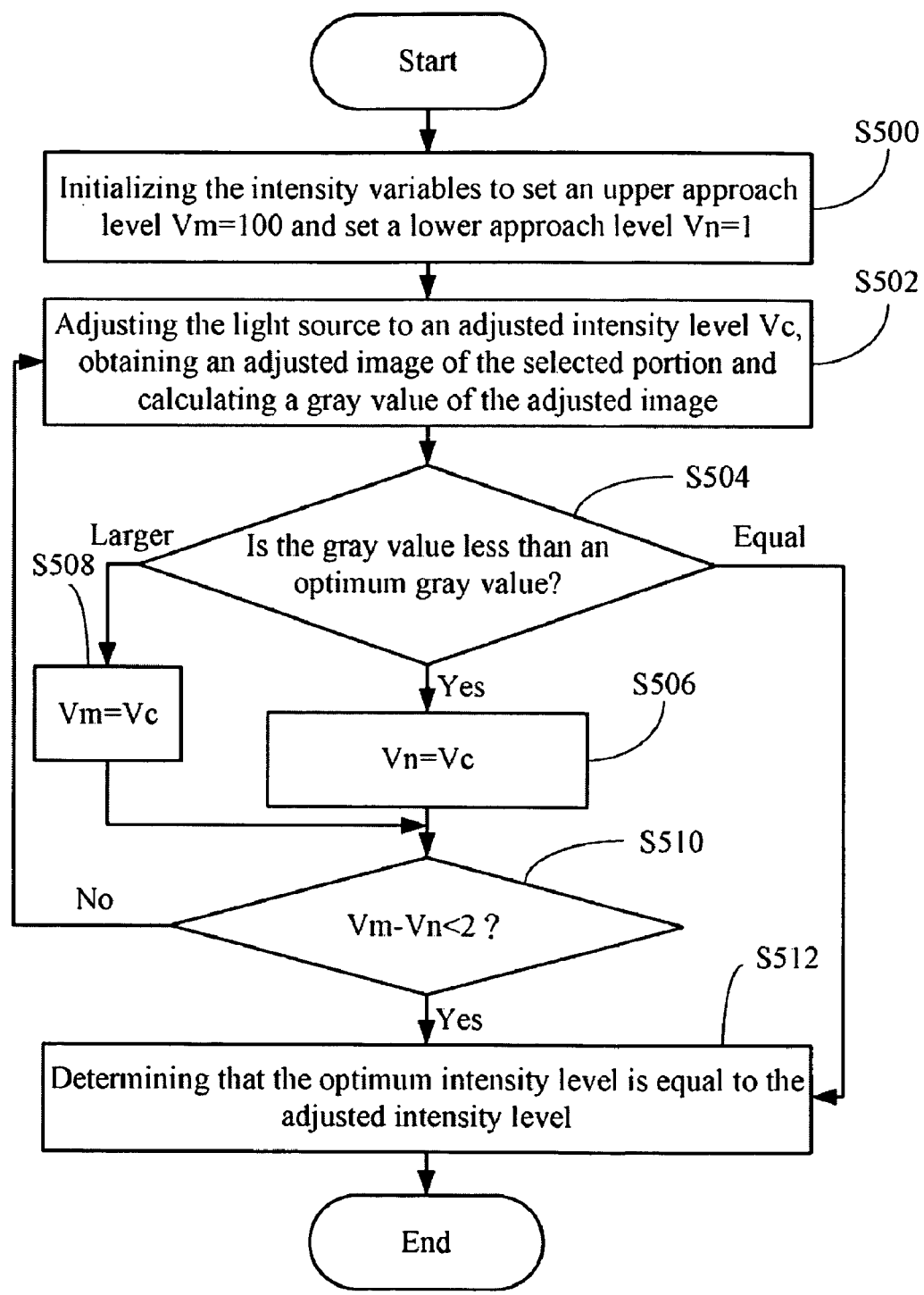
FIG. 5 is one block of FIG. 4 in detail, namely calculating an optimum intensity level of the backlight intensity by utilizing an iterative method.

FIG. 5 is a flowchart of block S408 of FIG. 4 in detail, namely calculating the optimum intensity level (symbolically depicted as "Vp") of the backlight intensity by utilizing the iterative method.

In block S500, the calculating module 302 initializes the intensity variables to set the upper approach level (symbolically depicted as "Vm") to the level 100, and to set the lower approach level (symbolically depicted as "Vn") to the level 1.

In block S502, the adjusting module 304 controls the light resource regulator 10 to adjust the backlight intensity of the light source 12 to an adjusted intensity level, the image processing module 300 obtains an adjusted image of the selected portion image based on the adjusted intensity level, and the calculating module 302 calculates a gray value of the adjusted image. In the embodiment, the adjusted intensity level (symbolically depicted as "Vc") is equal to one half of a sum value of the upper approach level Vm, and the lower approach level Vn, namely the adjusted intensity level Vc=(Vm+Vn)/2.

In block S504, the calculating module 302 determines whether the gray value of the adjusted image is less than an optimum gray value (symbolically depicted as "Gp") preset by the user. In the embodiment, the optimum gray value Gp is a middle value in the range from 0-255 gray levels, and is a gray value of the optimum profile image. The present embodiment gives an example that the optimum gray value Gp is equal to 125.

If the gray value equals the optimum gray value Gp, the flow directly enters block S512. If the gray value of the adjusted image is less than the optimum gray value Gp, in block S506, the calculating module 302 sets the adjusted intensity level Vc as the lower approach level Vn, and the flow may enter into block S510.

Otherwise, if the gray value of the adjusted image is greater than the optimum gray value Gp, in block S508, the calculating module 302 sets the adjusted intensity level Vc as the upper approach level Vm, and the flow may enter into block S510.

In block S510, the calculating module 302 determines whether a difference between the upper approach level Vm and the lower approach level Vn is less than a predetermined value preset by the user. In the embodiment, the predetermined value equals 2.

If the difference is no less than the predetermined value, in block S512, the calculating module 302 determines that the optimum intensity level Vp is equal to the adjusted intensity level Vc.

Otherwise, if the difference is less than the predetermined value, the flow may return block S502 to calculate the optimum intensity level Vp according to the above method. For example, if the adjusted intensity level Vc set in block S502 is equal to Vc1 and the gray value of the adjusted image is equal to Gc1, the calculating module 302 uses the formula Vc=(Vm+Vn)/2 to calculate an adjusted intensity level Vc2, and obtains a corresponding gray value Gc2 of the adjusted image (see FIG. 2), and then the calculating module 302 repeats the blocks from block S504 to block S510 till the optimum intensity level Vp is calculated.

Although certain inventive embodiments of the present disclosure have been specifically described, the present disclosure is not to be construed as being limited thereto. Various changes or modifications may be made to the present disclosure without departing from the scope and spirit of the present disclosure.

What is claimed is:

1. A computer-implemented method for adjusting backlight in measurement of a profile image of an object, the method comprising:

setting a light source of an image measuring machine to an original intensity level;

obtaining the profile image of the object on the image measuring machine, and performing a mean filter processing and a binary image processing on the profile image;

setting intensity variables to adjust backlight intensity of the light source, the intensity variables comprising an upper approach level and a lower approach level;

calculating an optimum intensity level of the backlight intensity utilizing an iterative method;

adjusting the backlight intensity of the light source to the optimum intensity level to obtain an optimum profile image of the object; and storing the optimum profile image and the optimum intensity level into a storage system.

2. The method according to claim 1, wherein the optimum profile image has a gray value that is a middle value in the range from 0-255 gray levels.

3. The method according to claim 1, wherein the light source comprises 101 intensity levels ranging from 0-100 intensity levels to reflect the backlight intensity, and wherein the original intensity level is in the range from the 0-100 intensity levels.

4. The method according to claim 3, wherein the calculating block comprises:

(a) initializing the intensity variables to set the upper approach level to the level 100 and set the lower approach level to the level 1;

(b) adjusting the backlight intensity of the light source to an adjusted intensity level, wherein the adjusted intensity level is equal to one half of a sum value of the upper approach level and the lower approach level;

(c) obtaining an adjusted image of the object based on the adjusted intensity level, and calculating a gray value of the adjusted image;

(d) determining whether the gray value of the adjusted image is less than an optimum gray value, wherein the optimum gray value is a gray value of the optimum profile image that is a middle value in the range from 0-255; and (e) determining that the optimum intensity level is equal to the adjusted intensity level if the gray value of the adjusted image is equal to the optimum gray value.

5. The method according to claim 4, wherein block (d) further comprises:

setting the adjusted intensity level as the lower approach level if the gray value of the adjusted image is less than the optimum gray value, or setting the adjusted intensity level as the upper approach level if the gray value of the adjusted image is greater than the optimum gray value;

determining whether a difference between the upper approach level and the lower approach level is less than a predetermined value; and returning block (b) if the difference is no less than the predetermined value, or determining that the optimum intensity level is equal to the adjusted intensity level if the difference is less than the predetermined value.

6. The method according to claim 5, wherein the predetermined value equals 2.

7. A computing system for adjusting backlight in measurement of a profile image of an object on an image measuring machine, the computing system comprising:

an image processing module configured for performing a mean filter processing and a binary image processing on the profile image of the object, after a light source of the image measuring machine is set to an original intensity level;

a calculating module configured for setting intensity variables to adjust backlight intensity of the light source, and using the intensity variables to calculate an optimum intensity level of the backlight intensity utilizing an iterative method;

an adjusting module configured for adjusting the backlight intensity of the light source to the optimum intensity level to obtain an optimum profile image of the object;

a reporting module configured for reporting and displaying the optimum profile image, and storing the optimum profile image and the optimum intensity level into a storage system; and at least one processor that executes the image processing module, the calculating module, the adjusting module, and the reporting module.

8. The system according to claim 7, wherein the light source comprises 101 intensity levels ranging from 0-100 intensity levels to reflect the backlight intensity, and wherein the original intensity level is in the range from the 0-100 intensity levels.

9. The system according to claim 7, wherein a gray value of the optimum profile image is a middle value in the range from 0-255 gray levels.

10. The system according to claim 7, wherein the intensity variables comprise an upper approach level and a lower approach level.

11. The system according to claim 10, wherein the iterative method is performed based on a formula: $Vc=(Vm+Vn)/2$, wherein Vc represents a current intensity level of the backlight intensity, Vm represents the upper approach level, and Vn represents the lower approach level.

12. The system according to claim 7, wherein the storage system is at least one of a hard disk drive, a compact disc, a digital video disc, and a tape drive.

13. A non-transitory computer-readable medium having stored thereon instructions for adjusting backlight in measurement of a profile image of an object, the computer-readable medium, when executed by a computer, causing the computer to perform a method, the method comprising:

setting a light source of an image measuring machine to an original intensity level;

obtaining the profile image of the object on the image measuring machine, and performing a mean filter processing and a binary image processing on the profile image;

setting intensity variables to adjust backlight intensity of the light source, the intensity variables comprising an upper approach level and a lower approach level;

calculating an optimum intensity level of the backlight intensity utilizing an iterative method;

adjusting the backlight intensity of the light source to the optimum intensity level to obtain an optimum profile image of the object; and storing the optimum profile image and the optimum intensity level into a storage system.

14. The non-transitory computer-readable medium according to claim 13, wherein a gray value of the optimum profile image is a middle value in the range from 0-255 gray levels.

15. The non-transitory computer-readable medium according to claim 13, wherein the light source comprises 101 intensity levels ranging from 0-100 intensity levels to reflect the backlight intensity, and wherein the original intensity level is in the range from the 0-100 intensity levels.

16. The non-transitory computer-readable medium according to claim 15, wherein the calculating block comprises:

(a) initializing the intensity variables to set the upper approach level to the level 100 and set the lower approach level to the level 1;

(b) adjusting the backlight intensity of the light source to an adjusted intensity level, wherein the adjusted intensity level is equal to one half of a sum value of the upper approach level and the lower approach level;

(c) obtaining an adjusted image of the object based on the adjusted intensity level, and calculating a gray value of the adjusted image;

(d) determining whether the gray value of the adjusted image is less than an optimum gray value, wherein the optimum gray value is a gray value of the optimum profile image that is a middle value in the range from 0-255; and (e) determining that the optimum intensity level is equal to the adjusted intensity level if the gray value of the adjusted image is equal to the optimum gray value.

17. The non-transitory computer-readable medium according to claim 16, wherein block (d) further comprises:

setting the adjusted intensity level as the lower approach level if the gray value of the adjusted image is less than the optimum gray value, or setting the adjusted intensity level as the upper approach level if the gray value of the adjusted image is greater than the optimum gray value;

determining whether a difference between the upper approach level and the lower approach level is less than a predetermined value; and returning block (b) if the difference is no less than the predetermined value, or determining that the optimum intensity level is equal to the adjusted intensity level if the difference is less than the predetermined value.

18. The non-transitory computer-readable medium according to claim 17, wherein the predetermined value equals 2.

19. The non-transitory computer-readable medium according to claim 13, wherein the storage system is at least one of a hard disk drive, a compact disc, a digital video disc, and a tape drive.

* * * * *